United States Patent [19]

Kobayashi et al.

[11] Patent Number: 4,978,612
[45] Date of Patent: Dec. 18, 1990

[54] ANALYTICAL ELEMENT FOR DETERMINATION OF HYDROGEN PEROXIDE AND ANALYTICAL METHOD USING THE SAME

[75] Inventors: Morio Kobayashi; Masakazu Sugao, both of Tokyo, Japan

[73] Assignee: Konica Corporation, Tokyo, Japan

[21] Appl. No.: 117,799

[22] Filed: Nov. 5, 1987

[30] Foreign Application Priority Data

Nov. 17, 1986 [JP] Japan .................. 61-273433

[51] Int. Cl.$^5$ .................. C12Q 1/61; C12Q 1/28; C12Q 1/26; C12Q 1/54
[52] U.S. Cl. .................. 435/10; 435/11; 435/14; 435/16; 435/25; 435/28; 435/805; 435/810; 436/169; 436/170; 422/56; 422/60; 422/61
[58] Field of Search .................. 435/28, 10, 11, 14, 435/16, 18, 25, 28, 805, 810; 436/66, 63, 169, 170; 422/56, 60, 61

[56] References Cited

U.S. PATENT DOCUMENTS

| | | | |
|---|---|---|---|
| 4,255,519 | 3/1981 | Terada et al. | 435/25 X |
| 4,278,439 | 7/1981 | White | 435/28 X |
| 4,418,037 | 11/1983 | Katsuyama et al. | 435/805 X |
| 4,460,684 | 7/1984 | Bauer | 435/805 X |
| 4,665,023 | 5/1987 | Deneke et al. | 435/28 |
| 4,672,029 | 6/1987 | Washburn et al. | 435/10 |
| 4,721,670 | 1/1988 | Osada et al. | 435/28 |
| 4,732,736 | 3/1988 | Kobayashi et al. | 435/28 X |
| 4,849,342 | 7/1989 | Ben-Michael | 435/28 X |

FOREIGN PATENT DOCUMENTS

| | | | |
|---|---|---|---|
| 0165588 | 12/1985 | European Pat. Off. | 435/28 |
| 0110197 | 7/1982 | Japan | 435/28 |
| 0126245 | 7/1984 | Japan | 435/28 |

Primary Examiner—Robert J. Warden
Assistant Examiner—Toni R. Scheiner
Attorney, Agent, or Firm—Frishauf, Holtz, Goodman & Woodward

[57] ABSTRACT

Disclosed is an analytical element for determination of hydrogen peroxide, which comprises using an analytical element containing a substance having the action of peroxidation, a compound represented by Formula (I) shown below, and an aromatic primary amine compound, or a salt thereof, capable of forming a dye through the coupling reaction with the compound represented by Formula (I) shown below: Formula (I)

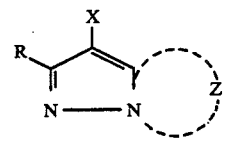

wherein Z represents a group of nonmetallic atoms necessary for forming a nitrogen-containing heterocyclic ring, which ring formed by Z may have a substituent; X represents a hydrogen atom or a group capable of being split off through the reaction with an oxidized product of the aromatic primary amine compound; and R represents a hydrogen atom or a substituent.

Disclosed is also an analytical method for determination of hydrogen peroxide by use of the above analytical element.

As described in the foregoing, the analytical element of this invention can exhibit the remarkable effect that the determination sensitivity can be greatly improved.

18 Claims, No Drawings

ANALYTICAL ELEMENT FOR DETERMINATION OF HYDROGEN PEROXIDE AND ANALYTICAL METHOD USING THE SAME

BACKGROUND OF THE INVENTION

This invention relates to an analytical element useful for determining hydrogen peroxide or a substance capable of forming hydrogen peroxide, in the presence of a substance having the action of peroxidation.

As a method for assaying glucose, cholesterol, uric acid and so forth, there has been generally used a method of determining target components by determining hydrogen peroxide formed by causing the corresponding oxidases, for example, glucose oxidase, cholesterol oxidase, uricase and so forth to act.

Well known as methods for determining these oxidases are methods in which a chromogen is changed into an oxidation type or one or two kinds of chromogen(s) is/are allowed to undergo oxidation condensation to carry out colorimetry in the presence of a substance having the action of peroxidation. Of these, for example, described in Japanese Unexamined Patent Publications No. 94653/1982, No. 94654/1982, No. 94655/1982, No. 94656/1982, etc. is a method in which, in a dry-type analytical element, a nondiffusion pyrazolone compound, non-diffusion acylacetamide compound, nondiffusion phenol compound or a nondiffusion naphthol compound is combined with an aromatic primary amine compound, or a salt thereof, capable of forming a dye through the coupling reaction with any of these compounds to determine hydrogen peroxide or a substance capable of forming hydrogen peroxide in the presence of a substance having the action of peroxidation.

The method using as a chromogen the combination of the compounds as mentioned above is useful as it can achieve a relatively higher determination sensitivity as compared with the methods using the conventionally known chromogens. However, because of very low concentration of the hydrogen peroxide to be determined when, for example, uric acid, creatinine, glutamate-oxaloacetate transaminase (GOT), glutamate-pyruvate transaminase (GPT) and so forth present in a low level in a biological liquid sample (for example, a serum) are derived to the hydrogen peroxide for its determination, it still can not be said to have achieved a sufficient discrimination sensitivity for determining these components.

SUMMARY OF THE INVENTION

An object of this invention is to provide an analytical element having a very good determination sensitivity in determining hydrogen peroxide or a substance capable of forming hydrogen peroxide, in the presence of a substance having the action of peroxidation.

The above object of this invention can be achieved by an analytical element for determination of hydrogen peroxide, containing a substance having the action of peroxidation, a compound represented by Formula (I) shown below, and an aromatic primary amine compound, or a salt thereof, capable of forming a dye through the coupling reaction with the compound represented by Formula (I) shown below.

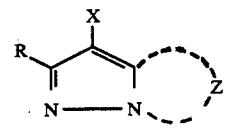

wherein Z represents a group of nonmetallic atoms necessary for forming a nitrogen-containing heterocyclic ring, which ring formed by Z may have a substituent; X represents a hydrogen atom or a group capable of being split off through the reaction with an oxidized product of the aromatic primary amine compound; and R represents a hydrogen atom or a substituent.

DESCRIPTION OF THE PREFERRED EMBODIMENTS

In the compound represented by the above Formula (I) according to this invention, there is no limitation for the substituent represented by R. However, it may typically include alkyl, aryl, anilino, acylamino, sulfonamide, alkylthio, arylthio, alkenyl and cycloalkyl groups, and, besides these, it may also include a halogen atom, and sulfonyl, sulfinyl, phosphonyl, acyl, carbamoyl, sulfamoyl, cyano, alkoxy, aryloxy, heterocyclic oxy, siloxy, acyloxy, carbamoyloxy, amino, alkylamino, imide, ureido, sulfamoylamino, alkoxycarbonylamino, aryloxycarbonylamino, alkoxycarbonyl, aryloxycarbonyl and heterocyclic thio groups, and also spiro compound residual groups, cross-linked organic hydrocarbon compound residual groups, etc.

The alkyl group represented by R may preferably include those having 1 to 32 carbon atoms, which may be of straight-chain or branched ones.

The aryl group represented by R may preferably include a phenyl group.

The acylamino group represented by R may include an alkyl carbonylamino group, an arylcarbonylamino group, etc.

The sulfonamide group represented by R may include an alkylsulfonylamino group, an arylsulfonylamino group, etc.

The alkyl component and the aryl component in the alkylthio group and the arylthio group represented by R may include the alkyl group and the aryl group represented by the above R, respectively.

The alkenyl group represented by R may preferably include those having 2 to 32 carbon atoms; and the cycloalkyl group, those having 3 to 12, particularly 5 to 7, carbon atoms. The alkenyl group may be of straight chain or branched ones.

The cycloalkenyl group represented by R may preferably include those having 3 to 12, particularly 5 to 7, carbon atoms.

The sulfonyl group represented by R may include an alkyl sulfonyl group, an aryl sulfonyl group, etc.;
the sulfinyl group may include an alkylsulfinyl group, an aryl sulfinyl group, etc.;
the phosphonyl group, an alkylphosphonyl group, an alkoxyphosphonyl group, an aryloxyphosphonyl group, an arylphosphonyl group, etc.;
the acyl group, an alkylcarbonyl group, an arylcarbonyl group, etc.;
the carbamoyl group, an alkylcarbamoyl group, an arylcarbamoyl group, etc.;
the sulfamoyl group, an alkylsulfamoyl group, an arylsulfamoyl group, etc.;

the acyloxy group, an alkylcarbonyloxy group, an arylcarbonyloxy group, etc.;

the carbamoyloxy group, an alkylcarbamoyloxy group, an arylcarbamoyloxy group, etc.;

the ureido group, an alkylureido group, an arylureido group, etc.;

the sulfamoylamino group, an alkylsulfamoylamino group, an arylsulfamoylamino group, etc.;

the heterocyclic ring group, preferably those of 5 to 7 members, specifically including a 2-furyl group, a 2-thienyl group, a 2-pyrimidinyl group, a 2-benzothiazolyl group, etc.;

the heterocyclic oxy group, preferably those having a heterocyclic group of 5 to 7 members, including, for example, a 3,4,5,6-tetrahydropyranyl-2-oxy group, a 1-phenyltetrazole-5-oxy group, etc.;

the heterocyclic thio group, preferably heterocyclic thio groups of 5 to 7 members, including, for example, a 2-pyridylthio group, a 2-benzothiazolylthio group, a 2,4-diphenoxy-1,3,5-triazole-6-thio group, etc.;

the siloxy group, a trimethylsiloxy group, a triethylsiloxy group, a dimethylbutylsiloxy group, etc.

the imide group, a succinimide group, a 3-heptadecylsuccinimide group, a phthalimide group, a glutarimide group, etc.;

the spiro compound residual group, spiro[3.3]heptan-1-yl, etc.; and the cross-linked organic hydrocarbon compound residual group, bicyclo[2.2.1]heptan-1-yl, tricyclo[3.1.1$^{3,7}$]decan-1-yl, 7,7-dimethyl-bicyclo[2.2.1-]heptan-1-yl, etc.

The group represented by X capable of being split off through the reaction with an oxidized product of the aromatic primary amine compound may include, for example, a halogen atom (a chlorine atom, a bromine atom, a fluorine atom, etc.) and alkoxy, aryloxy, heterocyclic oxy, acyloxy, sulfonyloxy, alkoxycarbonyloxy, aryloxycarbonyl, alkyloxalyloxy, alkoxyoxalyloxy, alkylthio, arylthio, heterocyclic thio, alkyloxythiocarbonylthio, acylamino, sulfonamide, N-atom-bonded nitrogen-containing heterocyclic ring, alkyloxycarbonylamino, aryloxycarbonylamino and carboxyl groups, a group of

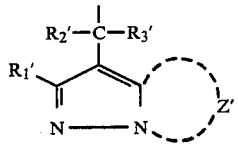

(wherein $R_1'$ has the same meaning as the above R; $Z'$ has the same meaning as the above Z; and $R_2'$ and $R_3'$ each represent a hydrogen atom, an aryl group, an alkyl group or a heterocyclic group), etc., but preferably includes a halogen atom, and particularly a chlorine atom.

The nitrogen-containing heterocyclic ring formed by Z or z' may include a pyrazole ring, an imidazole ring, a triazole ring or a tetrazole ring, etc., and the substituent the above ring may have may include those described for the above R.

The compound represented by Formula (I) can be further specifically represented, for example, by any of Formulas (II) to (VII) shown below.

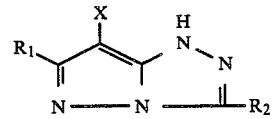
Formula (II):

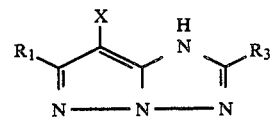
Formula (III):

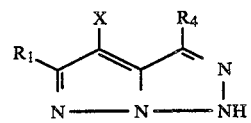
Formula (IV):

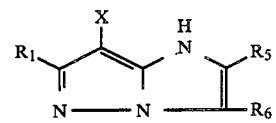
Formula (V):

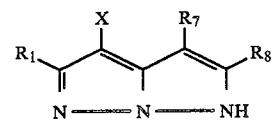
Formula (VI):

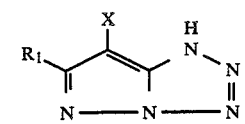
Formula (VII):

In the above Formulas (II) to (VII), $R_1$ to $R_8$ and X have the same meaning as the above R and X, respectively.

What is preferred in the compound of Formula (I) includes the compound represented by Formula (VIII) shown below.

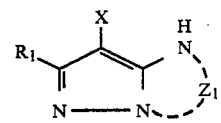

In the formula, $R_1$, X and $Z_1$ have the same meaning as R, X and Z in Formula (I), respectively.

A particularly preferable compound in the compounds represented respectively by Formulas (II) to (VII) is the compound represented by Formula (II).

Typical examples of the compound represented by Formula (I) according to this invention are shown below, but this invention is by no means limited by these.

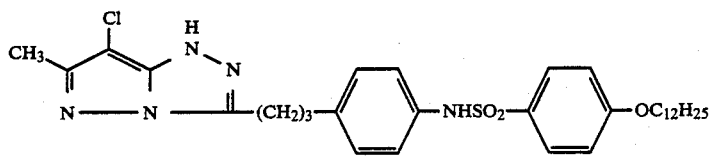
1-1
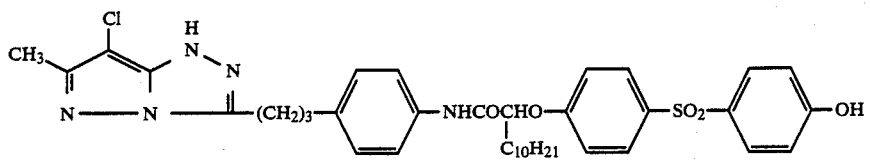
1-2
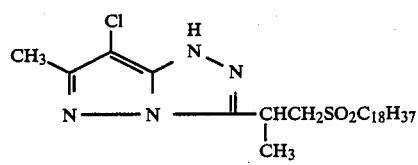
1-3
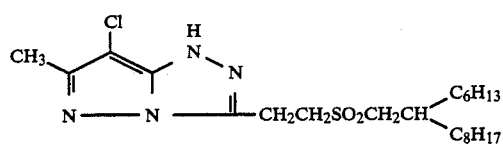
1-4
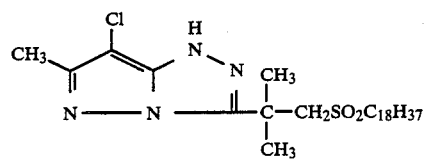
1-5
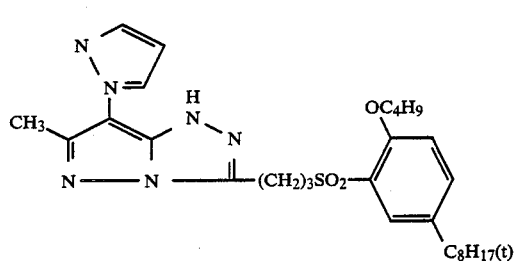
1-6
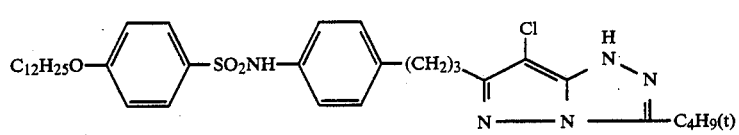
1-7
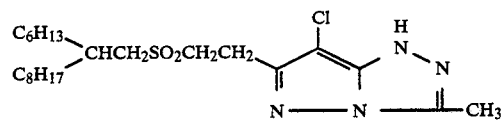
1-8
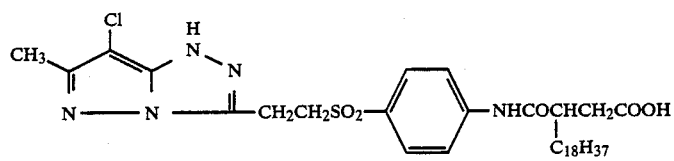
1-9

-continued
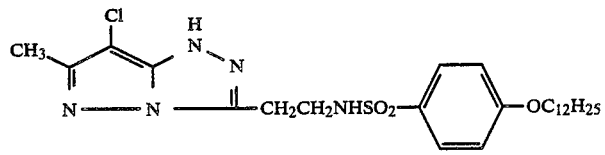
1-10
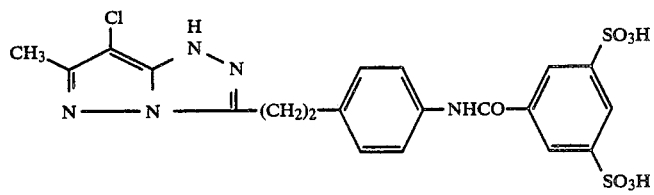
1-11
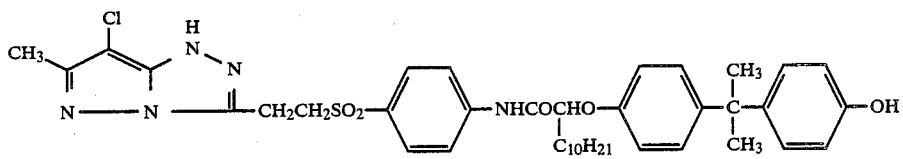
1-12
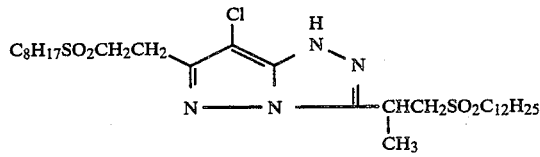
1-13
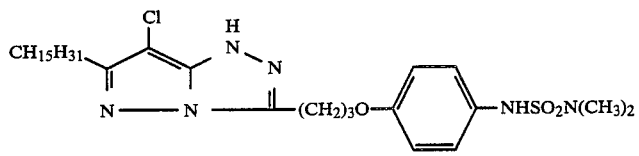
1-14
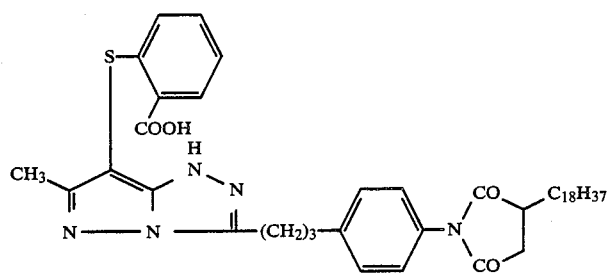
1-15
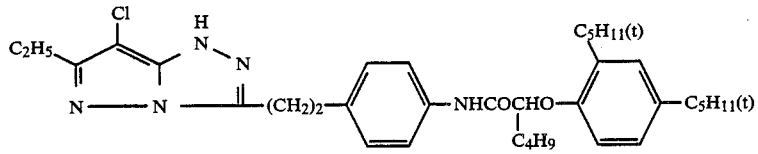
1-16
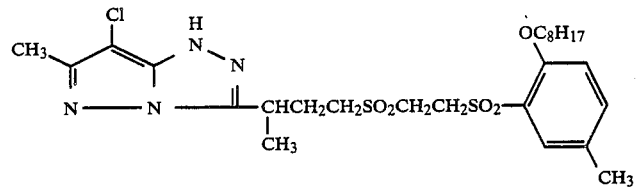
1-17

-continued
1-18
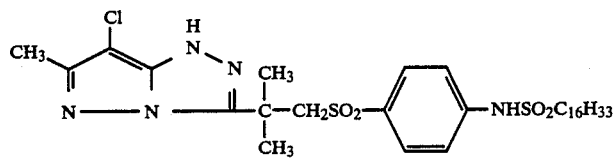
1-19
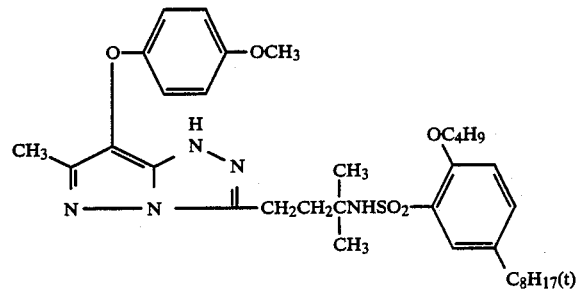
1-20
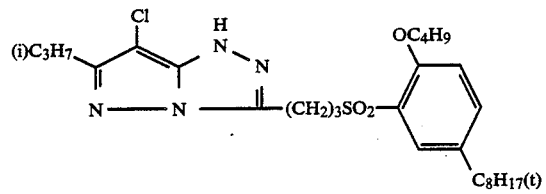
1-21
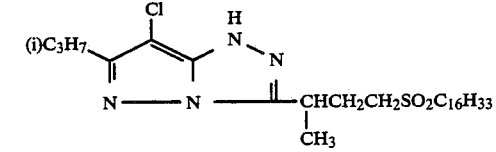
1-22
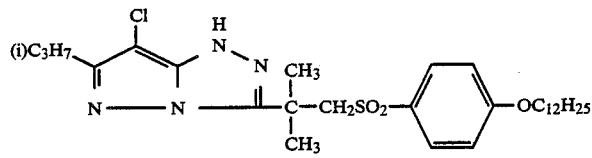
1-23
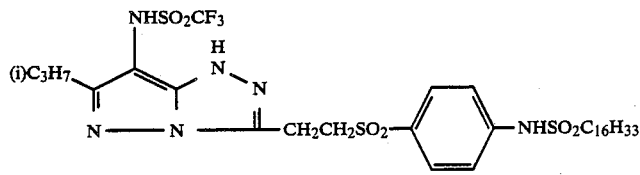
1-24
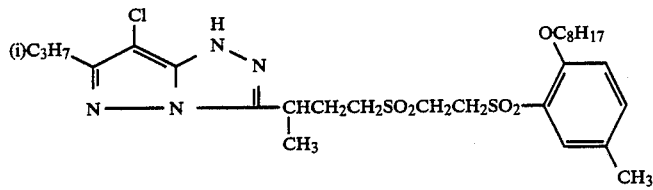
1-25
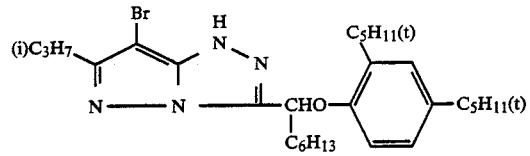

-continued
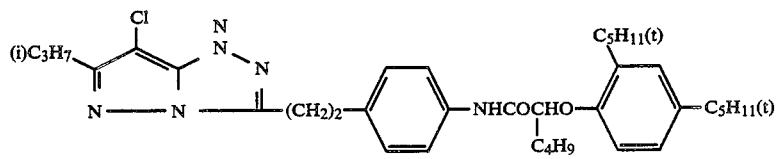
1-26
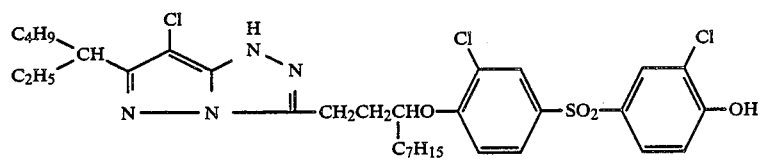
1-27
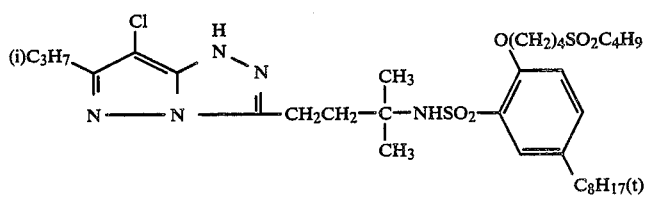
1-28
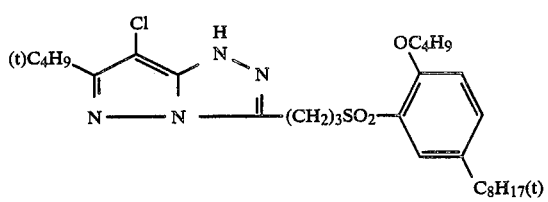
1-29
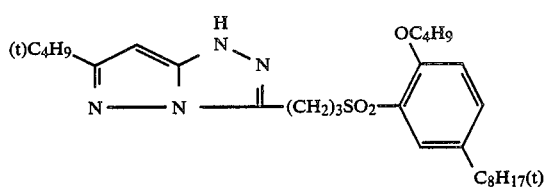
1-30
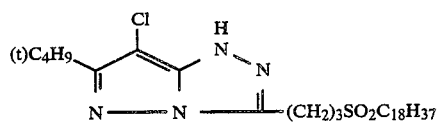
1-31
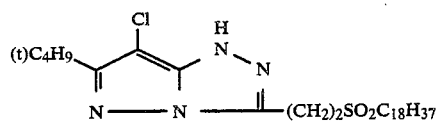
1-32
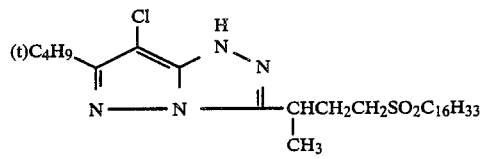
1-33
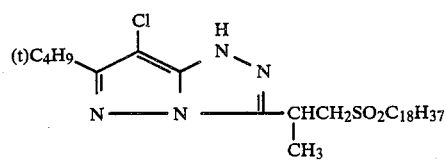
1-34

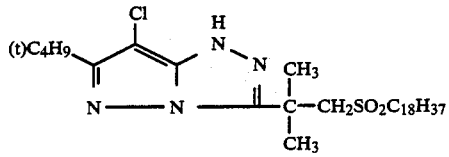
1-35
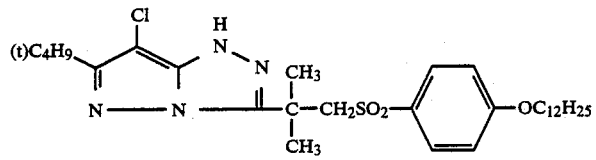
1-36
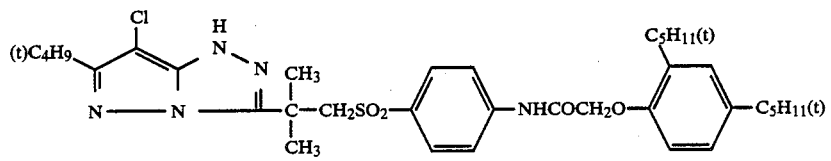
1-37
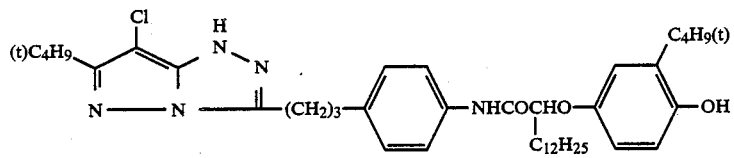
1-38
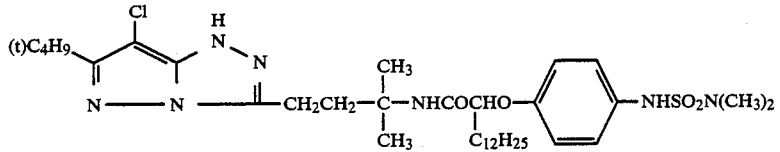
1-39
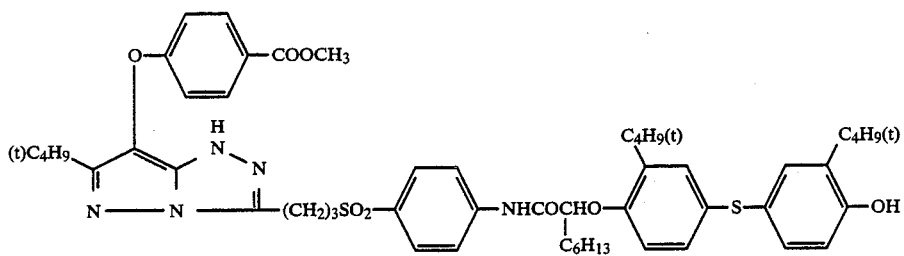
1-40
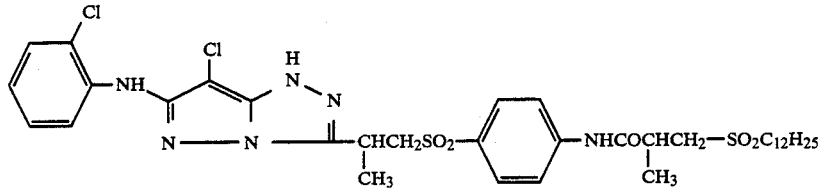
1-41
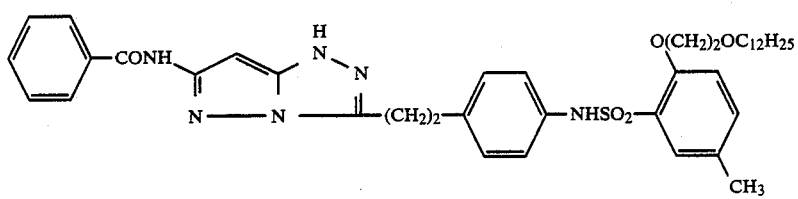
1-42

-continued
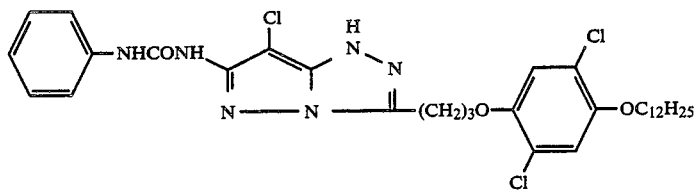
1-43
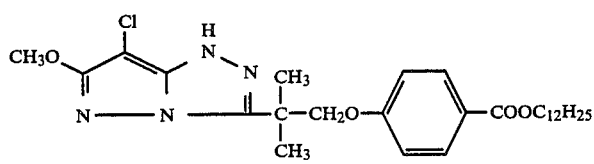
1-44
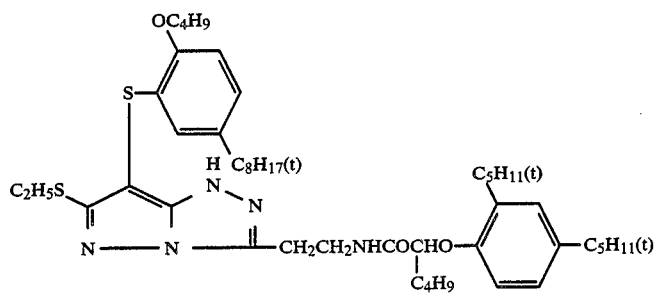
1-45
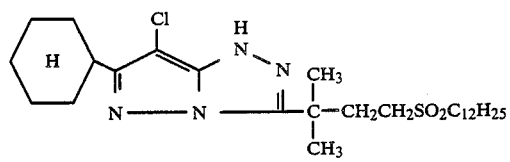
1-46
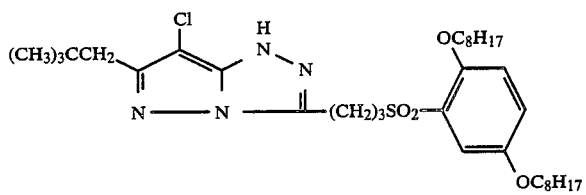
1-47
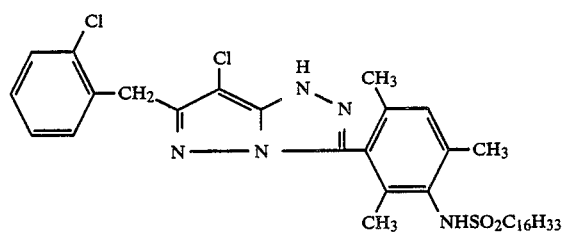
1-48
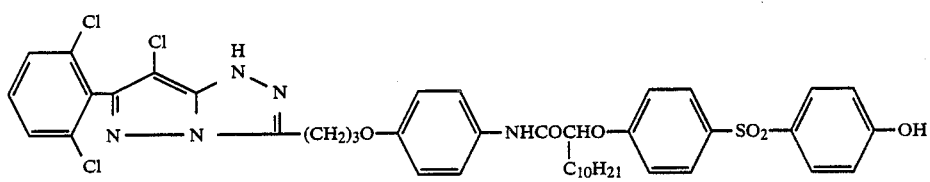
1-49

-continued
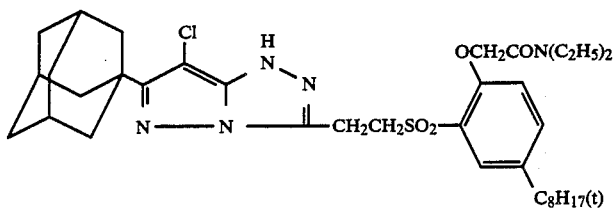
1-50
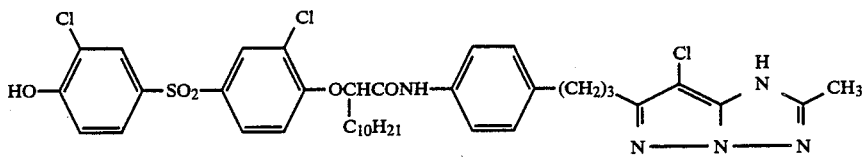
1-51
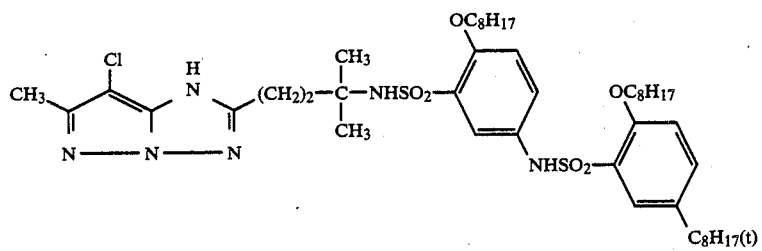
1-52
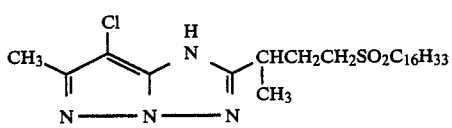
1-53
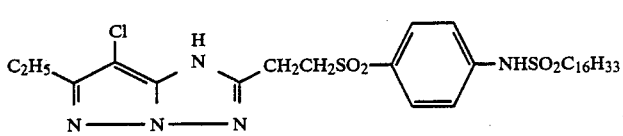
1-54
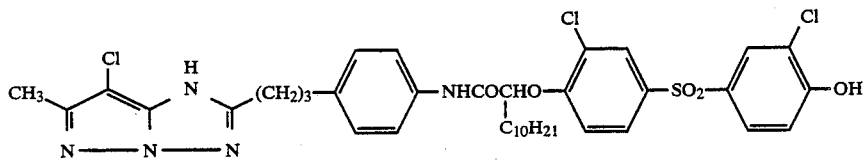
1-55
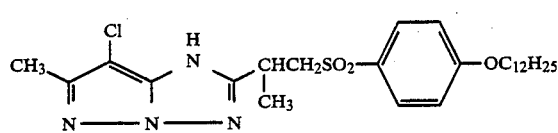
1-56
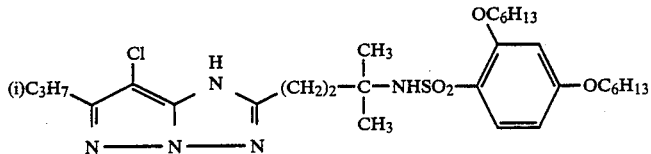
1-57
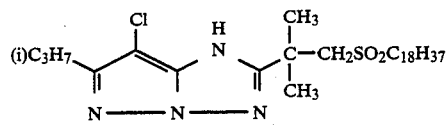
1-58

-continued
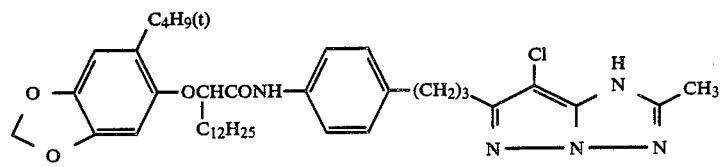
1-59
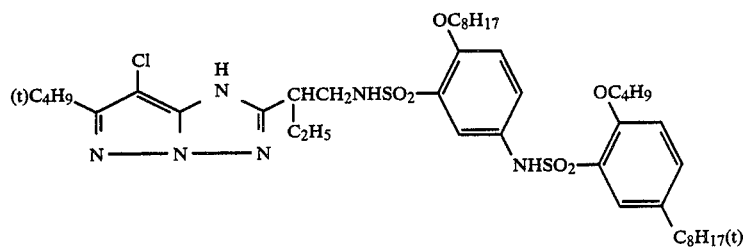
1-60
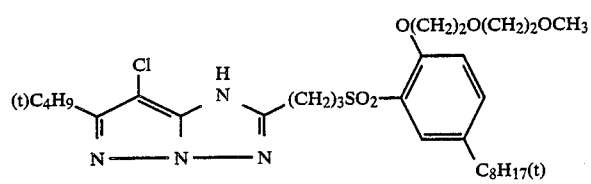
1-61
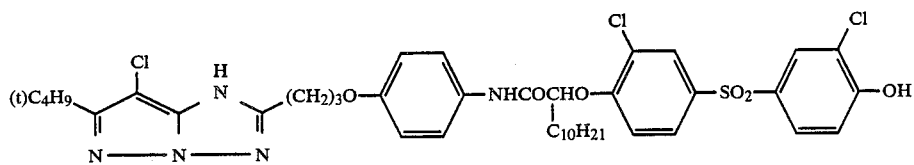
1-62
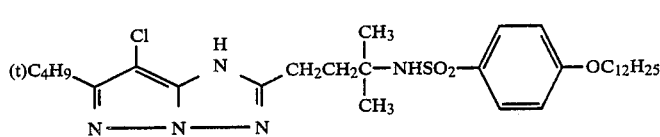
1-63
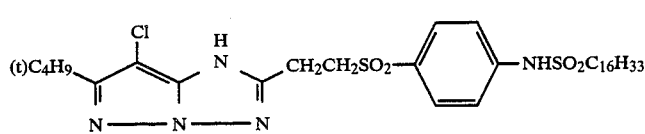
1-64
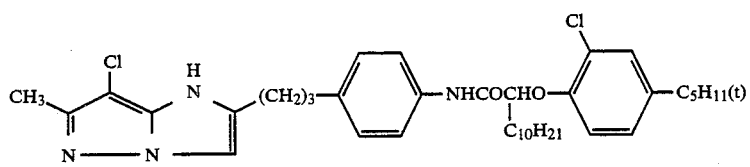
1-65
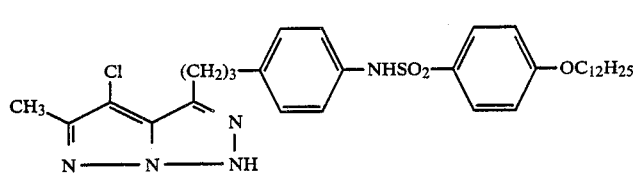
1-66

-continued

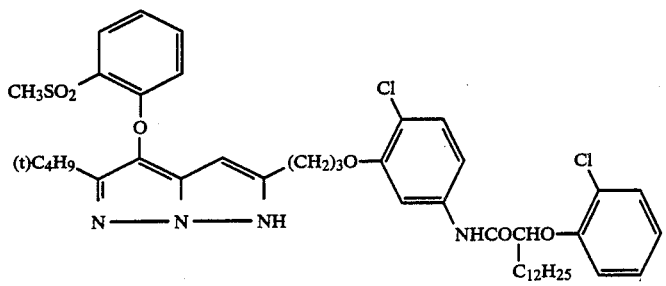

1-67

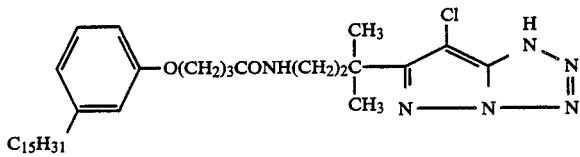

1-68

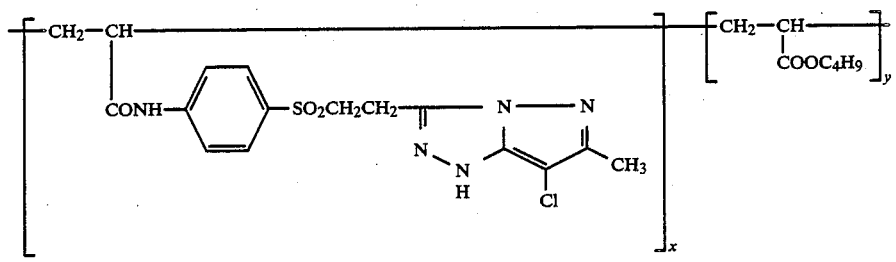

1-69 x:y = 50:50

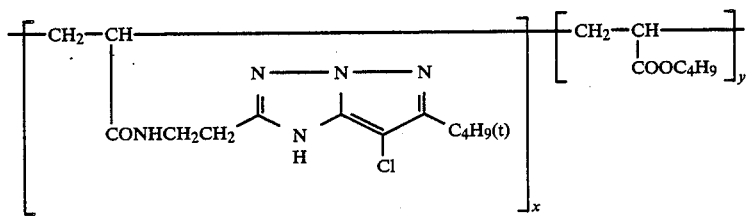

1-70 x:y = 50:50

In addition to the above typical examples, examples of the compound represented by Formula (I) according to this invention may also include the compounds other than those described in the present specification, among the compounds described on pages 66 to 122 in the specification of Japanese Unexamined Patent Publication No. 16639/1987.

The above compounds can be synthesized by making reference to Journal of The Chemical Society, Perkin I (1977), 2047–2052, U.S. Pat. No. 3,725,067, Japanese Unexamined Patent Publications No. 99437/1984, No. 42045/1983, No. 162548/1984, No. 171956/1984, No. 33552/1985, No. 43659/1985, No. 172982/1985 and No. 190779/1985, etc.

The aromatic primary amine compound according to this invention may include the known compounds widely used as color developing agents in various color photographic processes, including, for example, o- or p-aminophenol compounds and o- or p-phenylenediamine compounds. Preferably, it includes o- or p-phenylenediamine compounds, and, particularly preferably, p-phenylenediamine compounds.

The p-phenylenediamine compounds preferred in this invention include a compound represented by Formula (IX) shown below. Formula (IX):

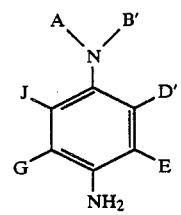

In the formula, A and B each represent a hydrogen atom or an alkyl group, and A and B' may form a heterocyclic ring together with a nitrogen atom. D', E, G and J each represent a hydrogen atom, a halogen atom, a hydroxyl group, an amino group, an alkoxy group, an acylamide group, an arylsulfonamide group, an alkylsulfonamide group or an alkyl group.

The alkyl group represented by A and B' may preferably include those having 1 to 6 carbon atoms, particularly preferably those having 1 to 4 carbon atoms. These alkyl groups may include those having a substituent, and the substituent may include, for example, an ureido group, a tetrahydrofurfuryl group, a carboxyl group, a methanesulfonamide group, a sulfo group, a methoxy group, a methoxyethoxy group, a methoxyethoxyethoxy group, a methoxytetraethoxy group, etc.

D', G and J each preferably represent a hydrogen atom, an alkoxy group, an alkylsulfonamide group and an arylsulfonamide group, more preferably, a hydrogen atom. E preferably represents a hydrogen atom, an alkyl group, an acylamide group, more preferably, an alkyl group having 1 to 3 carbon atoms. These alkyl groups may have a substituent same as the substituent for the alkyl group represented by the above A and B'. The compound represented by Formula (IX) is generally used in the form of a salt as being stabler than in a free state. The salt preferably includes, for example, salts of inorganic or organic acids such as hydrochloric acid, sulfuric acid, p-toluenesulfonic acid, sulfonic acid, sulfinic acids, sulfamic acids, carboxylic acids, phosphoric acids and boric acid. Particularly preferred are salts of hydrochloric acid, sulfuric acid and p-toluenesulfonic acid.

Typical examples of the aromatic primary amine compound according to this invention are shown below, but this invention is by no means limited by these.

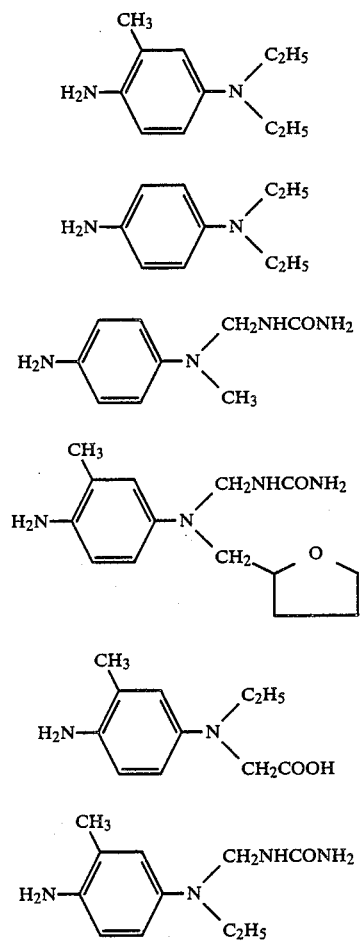

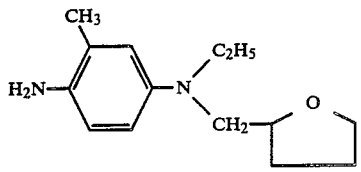

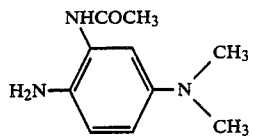

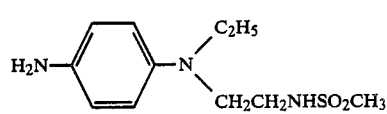

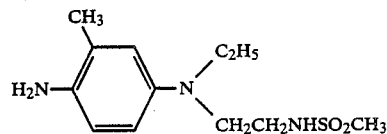

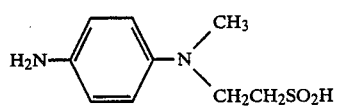

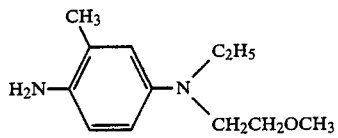

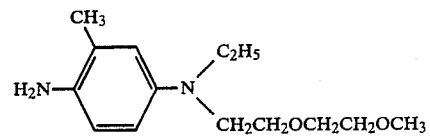

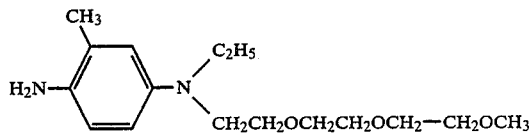

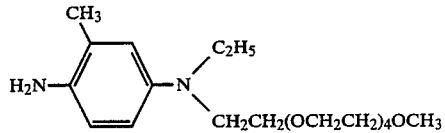

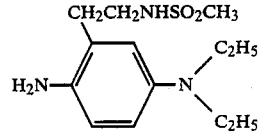

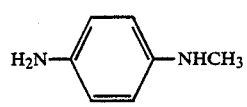

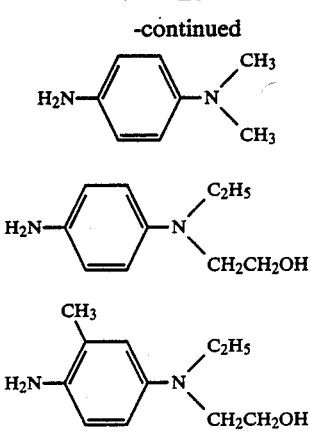

As the substance having the action of peroxidation according to this invention, there can be used various substances, typically including, for example, a peroxidase. The peroxidase is an enzyme catalyzing the reaction occurring when a hydrogen peroxide oxidizes other substance. This peroxidase is a conjugated protein generally containing iron porphyrin, and present in horseradishes, potatoes, sap in fig trees, turnips (vegetable peroxidase), cow's milk (lactoperoxidase) and white blood cells (verdoperoxidase). It is also present in microorganisms and can be obtained by extraction or fermentation.

Also usable in this invention is the synthetic peroxidase as disclosed in Acta Chemica Scandinavica, Vol. 4, pp.422–434, 1950, written by Theorell and Maehly. In addition to the peroxidase, also usable in this invention are methemoglobin, oxyhemoglobin, hemoglobin, alkaline hematin, hemin and hemin derivatives.

As substances capable of showing the action of peroxidation other than the enzymes, there can be used, for example, iron thiocyanate, iron stannate, ferrous ferocyanate, chromic salt adsorbed on silica gel (for example, potassium chromium sulfate), etc.

Among these, preferred is the peroxidase.

The analytical element of this invention refers to the dry type in which a reagent necessary for analysis is incorporated into the element in a dry state. The analytical elements of this type may include those comprising a single layer and using filter paper, a membrane filter or the like as the material for supporting a reagent (Japanese Patent Publication No. 4198/1961, U.S. Pat. No. 3,607,093, etc.), those comprising a net covered on two sheets of filter paper (Japanese Unexamined Patent Publication No. 151096/1984 and U.S. Pat. No. 3,526,480) and so forth.

The analytical element used in this invention may preferably also include an integral type multi-layer analytical element having on a liquid-impermeable and light-transmissive support at least one reagent layer and a porous spreading layer (Japanese Patent Publication No. 21677/1978, Japanese Unexamined Patent Publications No. 164359/1980, No. 90859/1980, No. 197466/1982, No. 101760/1982, No. 101761/1982. No. 90167/1983, etc.).

The above reagent layer can be provided as a layer by coating as a binder a water-soluble polymer or a hydrophilic and organic solvent soluble polymer on a support. The water-soluble polymer may include gelatin and gelatin derivatives such as phthalated gelatin, water-soluble cellulose derivatives such as hydroxyethyl cellulose and sodium carboxymethyl cellulose, polyvinyl alcohol, poly(N-vinyl pyrrolidone), polyacrylamide, polymethacrylamide, a copolymer of acrylamide with acrylate, poly(mono- or dialkyl-substituted)acrylamide, poly(mono- or dialkyl-substituted)methacrylamide, water-soluble copolymers of any of these, etc. Preferably used are gelatin, polyacrylamide, and a copolymer of acrylamide with acrylate. The hydrophilic and organic solvent soluble polymer binder may include poly(N-vinyl pyrrolidone), poly(N-vinyl imidazole), poly(N-vinyl triazole), derivatives of these or copolymers of any of these, cellulose derivatives such as ethyl cellulose, methyl cellulose, etc. These polymer binders are polymeric substances that are soluble chiefly in alcohols, for example, ethanol, propanol, butanol, etc. and are hydrophilic.

The above polymer binder can be arbitrarily selected depending on the specific components and analytical reaction thereof to be selected. When the analytical reaction to be selected is constituted of two or more reagents, the reagents may be contained in a same reagent layer by mixing them together, or two or more reagents may be contained as two or more separate reagent layers. These sometimes may be selected depending on the operational mechanism of the analytical reaction itself, and may take any constitution so long as there is no undesirable influence.

Thickness of the above reagent layer can be arbitrarily selected depending on what is desired, but may preferably be 1 to 200 μm, more preferably 5 to 100 μm.

The above porous spreading layer has (1) a function of distributing a given volume of a liquid sample in a reagent layer per unit area. Moreover, the layer is more preferable if it has further the functions as described in Japanese Patent Publication No. 21677/1978, i.e. (2) a function of removing a substance or factor that may inhibit the analytical reaction in a liquid sample and/or (3) a function of performing the background action by which the measuring light transmitting through a support can be reflected when a spectrophotometric analysis is carried out. Accordingly, the porous spreading layer according to this invention can comprise a layer having only the function of the above (1), or a layer having the functions of (2) and/or (3) in addition to the function (1). It is also possible to appropriately separate a plurality of functions including the function (1) and use an additional layer for each of the functions. It is further possible to use, among the functions (1), (2) and (3), a layer having any of the two functions and a layer having the remaining one function in combination. For example, such a spreading layer may include the spreading layer comprising a non-fibrous porous medium called a blush polymer comprising titanium dioxide and cellulose diacetate as described in the aforesaid Japanese Patent Publication No. 21677/1978, the spreading layer comprising a fabric having been made hydrophilic as described in Japanese Unexamined Patent Publication No. 164356/1980, the spreading layer having a fibrous structure as described in Japanese Unexamined Patent Publications No.94658/1982, No. 125847/1982, No. 197466/1982, No. 70161/1983, and the spreading layer having the structure of a particulate aggregate as described in Japanese Unexamined Patent Publication No. 90167/1983. Among these, particularly useful as a material capable of speedily transporting the blood cell part also are the spreading layer having a fibrous structure and the spreading layer having the structure of a particulate aggregate. The thickness of the spreading layer in the analytical element of this invention should be selected depending on its voids, but may preferably be about 100 to 600 μm, more preferably about 150 to 400 μm. The voids may preferably be about 20 to 85 %.

Similar to the case of the aforesaid reagent layer, the above porous spreading layer can also contain a reagent capable of participating directly or indirectly in the specific components, depending on the specific components and analytical reaction thereof to be selected.

As other additional additives, there can be optionally added various additives including, for example, preservatives, surface active agents, etc.

In particular, the surface active agents can be effectively used for controlling the rate of permeation when a liquid sample is applied on the analytical element of this invention.

As usable surface active agents, the surface active agents can be used regardless of being ionic (anionic or cationic) or being nonionic, but nonionic surface active agents can be effectively used. Example of the nonionic surface active agents may include polyalkylene glycol derivatives of alkyl-substituted phenols such as 2,5-di-t-butylphenoxypolyethylene glycol, p-octylohenoxypolyethylene glycol and p-isononylphenoxypolyethylene glycol; polyalkylene glycol esters of higher aliphatic acids; etc. These surface active agents have the effect of controlling the rate of permeation of a sample liquid to the reagent layer and at the same time suppressing the occurrence of the undesirable "chromatography phenomenon".

The above surface active agent can be used in an amount widely selected, and can be used in an amount of 25 % by weight to 0.005 % by weight, preferably 15 % by weight to 0.05 % by weight.

The above-mentioned liquid impermeable and light transmissive support (hereinafter called the support according to this invention) has no limitation in its kind so long as it is liquid-impermeable and at the same time light-transmissive. For example, there can be not only various polymer materials such as cellulose acetate, polyethylene terephthalate, polycarbonate or polystyrene, but also inorganic materials such as glass. The support according to this invention may have any thickness, but may preferably be 5 to 250 μm in thickness. One side of the observation side of the support according to this invention can be worked out as desired depending on the purpose. It is further possible to use, as occasion demands, a light-transmissive subbing layer on the support face on the side on which the reagent layer is laminated, so that the adhesion between the reagent layer and the support can be improved.

The above integral type multi-layer analytical element may be optionally provided with, for example, the reflective layer and the subbing layer as described in U.S. Pat. No. 3,992,158, the radiation-blocking layer as described in U.S. Pat. No. 4,042,335, the barrier layer as described in U.S. Pat. No. 4,066,403, the migration-blocking layer as described in U.S. Pat. No. 4,166,093, the scavenger layer as described in Japanese Unexamined Pat. Publication No. 90859/1980, and the rupturable pod-like member(s) as described in U.S. Pat. No. 4,110,079, which can be used in any combination to take any desired constitution according to the purpose of this invention.

These various layers of the analytical element can be laminated in succession on the support according to this invention, in line with the desired constitution and by appropriately selecting a slide hopper coating method, an extrusion coating method, a dip coating method, etc. conventionally used in the photographic industry, to provide by coating, the layers with any desired thickness.

Methods for adding the compound represented by Formula (I) of this invention in the solution for forming the analytical element according to this invention, can be appropriately selected depending on the chemical structure or the like of the above compound. For example, there can be used various methods such as a method in which the compound is added by dissolving it in water, an aqueous alkaline solution, an aqueous buffer solution or an organic solvent, a solid dispersion method, a latex dispersion method and an oil-in-water type emulsification dispersion method.

Applicable as the oil-in-water type emulsification dispersion method is a method in which the hydrophobic additives such as couplers conventionally known in the photographic industry are dispersed, which can be generally used by dissolving them in a high-boiling solvent and/or a low-boiling solvent, and mixing the resulting solution with an aqueous solution containing a hydrophilic colloid such as gelatin containing an anionic surface active agent and/or a nonionic surface active agent, followed by emulsification dispersion with use of a high speed rotary mixer, a colloid mill, a flow jet mixer or an ultrasonic dispersion device.

The high-boiling solvent may include, for example, organic acid amides, carbamates, esters, ketones, urea derivatives, etc., specifically including di-n-butyl phthalate, tricresyl phosphate, triphenyl phosphate, di-iso-octyl phthalate, di-n-butyl cebacate, tri-n-hexyl phosphate, N,N-diethylcaprylamide, N,N-diethyllaurylamide, n-pentadecyl phenyl ether, dioctyl phthalate, n-nonylphenol, 3-pentadecyl phenyl ethyl ether, 2,5-di-sec-amylphenyl butyl ether, monophenyl-di-o-chlorophenyl phosphate, fluoroparaffin, etc. Among these, preferred are dialkyl phthalates, particularly, those comprising an alkyl group having 1 to 6 carbon atoms.

The low-boiling solvent may include, for example, methyl acetate, ethyl acetate, propyl acetate, butyl acetate, butyl propionate, cyclohexanol, diethylene glycol monoacetate, nitromethane, carbon tetrachloride, chloroform, cyclohexane, tetrahydrofuran, methyl alcohol, acetonitrile, N,N-dimethylformamide, dioxane, methyl ethyl ketone, etc.

The anionic surface active agent may include, for example, alkylbenzenesulfonic acid, alkylnaphthalenesulfonic acid, etc., and the nonionic surface active agent may include, for example, sorbitan sesquioleate, sorbitan monolaurate, et.

As methods for adding the aromatic primary amine compound or a salt thereof according to this invention in the solution for forming the analytical element according to this invention, there can be used various methods such as a method in which it is added by dissolving it in water, an aqueous buffer solution or an organic solvent, or a solid dispersion method.

In addition to the above-mentioned substance having the action of peroxidation, compound represented by Formula (I) and aromatic primary amine compound or a salt thereof, the analytical element of this invention can contain various reagents such as an oxidase capable of forming hydrogen peroxide and other enzymes, substrates, buffers, preservatives, surface active agents and hardening agents depending on the kind of the component to be analyzed.

The oxidase capable of forming hydrogen peroxide may include, for example, various enzymes such as glucose oxidase, uricase, cholesterol oxidase, glycerol oxidase, glycerin-3-phosphate oxidase, sarcosine oxidase, pyruvate oxidase, D-(or L-)amino acid oxidase, L-gulono-γ-lactone oxidase, L- (or D-)-hydroxyacid oxidase, pyridoxine oxidase, hexose oxidase, o-aminophenol oxidase, amine oxidase (containing pyridoxal, or containing flavin), xanthine oxidase, alcohol oxidase, ethanolamine oxidase, choline oxidase, acyl CoA oxidase, sulphite oxidase, ascorbate oxidase, etc.

The substance having the action of peroxidation according to this invention can be used in an amount widely selected. For example, in the case of peroxidase, it can be used in the range of 100 to 1,000,000 $U/m^2$, preferably 1,000 to 100,000 $U/m^2$.

The compound represented by Formula (I) according to this invention can be used in an amount widely selected, and can be used in the range of 0.1 to 100 $mmol/m^2$, preferably 0.5 to 50 $mmol/m^2$.

The aromatic primary amine compound according to this invention can be used in an amount widely selected, and can be used in the range of 0.005 to 100 $mmol/m^2$, preferably 0.01 to 50 $mmol/m^2$.

In the analytical element of this invention, the hydrogen peroxide or the hydrogen peroxide formed by the action of an oxidase oxidizes the aromatic primary amine compound according to this invention by the action of the substance having the action of peroxidation. An oxidized product formed as a result, of the aromatic primary amine compound undergoes a coupling reaction with the compound represented by Formula (I) according to this invention to form a dye. The dye thus formed has principal visible absorption at 500 to 600 nm and can produce a color in a very high sensitivity. Accordingly, the analytical element of this invention can sharply react also to trace components in a specimen, e.g., a human serum (for example, uric acid, creatinine, GOT, GPT, etc.), and thus can be particularly useful for the determination of the trace components.

In this invention, the substance having the action of peroxidation, compound represented by Formula (I) and aromatic primary amine compound according to this invention can be contained, in the case, for example, of the integral type multi-layer analytical element, in any layers including the reagent layer, the porous spreading layer and other layers, but preferably the compound represented by Formula (I) and the aromatic primary amine compound may be respectively separated and contained in different layers. For example, a preferred embodiment is such that the substance having the action of peroxidation and the compound represented by Formula (I) are contained in one reagent layer and the aromatic primary amine compound is contained in another reagent layer or in a porous spreading layer.

To determine the hydrogen peroxide or the substance capable of forming hydrogen peroxide with use of the analytical element of this invention, the analytical element may be dipped in a specimen, i.e., a liquid sample, or the liquid sample may be dropwise applied on the analytical element, to carry out the determination by reflection spectrophotometry according to an initial speed method or a reaction end point method. When the determinations thus obtained conform to calibration curves prepared beforehand, the quantity of one hydrogen peroxide or the substance capable of forming hydrogen peroxide can be determined.

The liquid sample to be applied in the analytical element of this invention may be any of biological or non-biological liquid sample so long as it contains the hydrogen peroxide or the substance capable of forming hydrogen peroxide. For example, it may include blood (including plasma and serum), lymph, urine, etc.

The liquid sample may be used in any amount so long as the amount is not less than the amount at which, in the case of a reagent strip, an absorptive carrier containing a reagent can be sufficiently impregnated with the liquid sample. On the other hand, it may be used in any amount also in the case of the integral type multi-layer analytical element, but preferably in an amount of about 50 μl to about 5 μl, more preferably about 20 μl to about 5 μl. It is generally preferred to use about 10 μl of the liquid sample.

This invention will be described below in greater detail by giving Examples.

EXAMPLE 1

(Uric acid analytical element)

On a transparent polyethylene terephthalate film having been subjected to a subbing treatment and having a film thickness of 180 μm, a reagent layer having the composition as shown in Table 1, an intermediate layer and a spreading layer each having the composition shown below were provided in succession to produce each of analytical elements 1 to 5 of this invention and comparative analytical element 1 as shown in Table 2.

TABLE 1

|  |  | Reagent layer | | | | | |
|---|---|---|---|---|---|---|---|
|  |  | R-1 | R-2 | R-3 | R-4 | R-5 | R-6 |
| Compound of the invention 1-4 | (g/m²) | 2.05 | — | — | — | — | — |
| Compound of the invention 1-5 | (g/m²) | — | 3.30 | — | — | — | — |
| Compound of the invention 1-8 | (g/m²) | — | — | 2.95 | — | — | — |
| Compound of the invention 1-20 | (g/m²) | — | — | — | 3.44 | — | — |
| Compound of the invention 1-34 | (g/m²) | — | — | — | — | 3.47 | — |
| Comparative compound (1) | (g/m²) | — | — | — | — | — | 4.60 |
| Dibutyl phthalate | (g/m²) | 1.55 | 1.73 | 1.55 | 1.81 | 1.82 | 2.42 |
| Gelatin | (g/m²) | 19.0 | 19.0 | 19.0 | 19.0 | 19.0 | 19.0 |
| Uricase | (U/m²) | 300 | 300 | 300 | 300 | 300 | 300 |
| Peroxidase | (U/m²) | 9,000 | 9,000 | 9,000 | 9,000 | 9,000 | 9,000 |
| Ascorbate oxidase | (U/m²) | 7,500 | 7,500 | 7,500 | 7,500 | 7,500 | 7,500 |
| Borate buffer, pH 8.5 | (g/m²) | 4.25 | 4.25 | 4.25 | 4.25 | 4.25 | 4.25 |
| Sodium triisopropylnaphthalenesulfonate | (g/m²) | 0.86 | 0.86 | 0.86 | 0.86 | 0.86 | 0.86 |
| 1,2-Bis(vinylsulfonyl)ethane | (g/m²) | 0.10 | 0.10 | 0.10 | 0.10 | 0.10 | 0.10 |

Comparative compound (1):

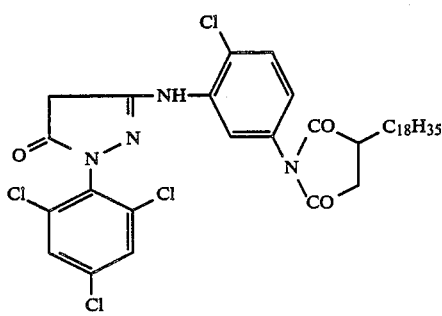

*1) All of compounds 1-4, 1-5, 1-8, 1-20, 1-34 of this invention and comparative compound (1) were used by dissolving each in ethyl acetate and dibutyl phthalate, and adding the resulting solution in an aqueous solution of sodium triisopropylnaphthalenesulfonate and gelatin, followed by ultrasonic dispersion.

*2) Ascorbate oxidase used originated from a cucumber.

Intermediate layer (I-1):

| Intermediate layer (I-1): | |
|---|---|
| N-vinyl pyrrolidone/vinyl acetate copolymer (weight ratio: 2:8) | 1.25 g/m² |
| Spreading layer (S-1): | |
| Fiber for filter paper material (available from Toyo Roshi K.K.; 40 to 100 mesh) | 91.0 g/m² |
| Styrene/glycidyl methacrylate copolymer (weight ratio: 9:1) | 23.0 g/m² |
| Triton X-100 | 9.1 g/m² |
| Compound 2-16 of this invention (hydrochloride) | 0.11 g/m² |
| Dimedone | 1.35 g/m² |
| Ascorbate oxidase | 7,500 U/m² |
| Cow's serum albumin | 1.10 g/m² |

*3) The above spreading layer was provided by coating, with use of xylene. Compound 2-16 of this invention (p-toluenesulfonate) and dimedone were coated by dissolving them in methanol followed by addition and dispersion.

*4) Ascorbate oxidase (originating from a cucumber) were dissolved in water together with cow's serum albumin and coated by adding fine powder obtained after the resulting solution was freeze-dried.

TABLE 2

| Analytical element number | Reagant layer | Intermediate layer | Spreading layer |
|---|---|---|---|
| Analytical element of the invention - 1 | R - 1 | I - 1 | S - 1 |

TABLE 2-continued

| Analytical element number | Reagant layer | Intermediate layer | Spreading layer |
|---|---|---|---|
| Analytical element of the invention - 2 | R - 2 | I - 1 | S - 1 |
| Analytical element of the invention - 3 | R - 3 | I - 1 | S - 1 |
| Analytical element of the invention - 4 | R - 4 | I - 1 | S - 1 |
| Analytical element of the invention - 5 | R - 5 | I - 1 | S - 1 |
| Comparative analytical element - 1 | R - 6 | I - 1 | S - 1 |

With regard to analytical elements 1 to 5 of this invention and comparative analytical element 1, 10 μl each of human serums having different uric acid concentration was dropwise applied on the spreading layers and, after incubation for 7 minutes at 37° C., the reflection density was measured from the support side with use of a filter of 546 nm to obtain the results shown in Table 3.

TABLE 3

| Uric acid concentration (mg/dl) | 3 | 7 | 12 | 15 |
|---|---|---|---|---|
| Analytical element of the invention - 1 | 0.54 | 0.85 | 1.12 | 1.24 |
| Analytical element of the invention - 2 | 0.52 | 0.80 | 1.03 | 1.14 |
| Analytical element of the invention - 3 | 0.53 | 0.83 | 1.10 | 1.22 |
| Analytical element of the invention - 4 | 0.51 | 0.81 | 1.04 | 1.15 |
| Analytical element of the invention - 5 | 0.52 | 0.79 | 1.02 | 1.12 |
| Comparative analytical element - 1 | 0.49 | 0.64 | 0.77 | 0.81 |

As will be clear from the results shown in the above Table 3, it can be understood that analytical elements 1 to 5 of this invention show better color density difference against the difference in the uric acid concentration as compared with comparative analytical element 1, proving a higher discrimination ability or determination sensitivity.

EXAMPLE 2

(Uric acid analytical element)

On a transparent polyethylene terephthalate film having been subjected to a subbing treatment and having a film thickness of 180 μm, a reagent layer having the composition as shown in Table 4, an intermediate layer and a spreading layer each having the composition shown below were provided in succession to produce each of analytical elements 6 to 10 of this invention and comparative analytical element 2 as shown in Table 5.

TABLE 4

| | | Reagent layer | | | | | |
|---|---|---|---|---|---|---|---|
| | | R-7 | R-8 | R-9 | R-10 | R-11 | R-12 |
| Compound of the invention 1-2 | (g/m²) | 4.49 | — | — | — | — | — |
| Compound of the invention 1-4 | (g/m²) | — | 2.95 | — | — | — | — |
| Compound of the invention 1-51 | (g/m²) | — | — | 4.92 | — | — | — |
| Compound of the invention 1-53 | (g/m²) | — | — | — | 3.12 | — | — |
| Compound of the invention 1-66 | (g/m²) | — | — | — | — | 3.83 | — |
| Comparative compound (2) | (g/m²) | — | — | — | — | — | 3.09 |
| Dibutyl phthalate | (g/m²) | 2.25 | 1.48 | 2.46 | 1.56 | 1.92 | 1.55 |
| Gelatin | (g/m²) | 19.0 | 19.0 | 19.0 | 19.0 | 19.0 | 19.0 |
| Uricase | (U/m²) | 6,000 | 6,000 | 6,000 | 6,000 | 6,000 | 6,000 |
| Borate buffer, pH 8.5 | (g/m²) | 4.25 | 4.25 | 4.25 | 4.25 | 4.25 | 4.25 |
| Sodium triisopropylnaphthalene- | (g/m²) | 0.86 | 0.86 | 0.86 | 0.86 | 0.86 | 0.86 |

TABLE 4-continued

| | | Reagent layer | | | | | |
|---|---|---|---|---|---|---|---|
| | | R-7 | R-8 | R-9 | R-10 | R-11 | R-12 |
| sulfonate | | | | | | | |
| 1,2-Bis(vinylsulfonyl)ethane | (g/m$^2$) | 0.10 | 0.10 | 0.10 | 0.10 | 0.10 | 0.10 |

Comparative compound (2)

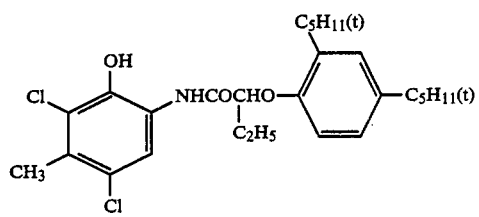

*5) All of compounds 1-2, 1-4, 1-51, 1-53 and 1-66 and comparative compound (2) were used by dispersing them in the same procedures as those described in Example 1.

Intermediate layer (I-2):

| Intermediate layer (I-2): | |
|---|---|
| N-vinyl pyrrolidone/vinyl acetate copolymer (weight ratio: 7:3) | 1.25 g/m$^2$ |
| Spreading layer (S-2): | |
| Fiber for filter paper material (available from Toyo Roshi K.K.; 40 to 100 mesh) | 91.0 g/m$^2$ |
| | 91.0 g/m2 |
| Styrene/glycidyl methacrylate copolymer (weight ratio: 9:1) | 23.0 g/m$^2$ |
| Triton X-100 | 9.1 g/m$^2$ |
| Compound 2-20 of this invention (sulfate) | 0.06 g/m$^2$ |
| Dimedone | 1.35 g/m$^2$ |
| Ascorbate oxidase *(4) | 20,000 U/m$^2$ |
| Cow's serum albumin *(4) | 2.5 g/m$^2$ |

*6) The above spreading layer was provided by coating, with use of a xylene solvent. Compound 2-20 (sulfate) of this invention and dimedone were coated by dissolving them in methanol followed by addition and dispersion.

TABLE 5

| Analytical element number | Reagent layer | Intermediate layer | Spreading layer |
|---|---|---|---|
| Analytical element | R - 7 | I - 2 | S - 2 |

TABLE 5-continued

| Analytical element number | Reagent layer | Intermediate layer | Spreading layer |
|---|---|---|---|
| of the invention - 6 | | | |
| Analytical element of the invention - 7 | R - 8 | I - 2 | S - 2 |
| Analytical element of the invention - 8 | R - 9 | I - 2 | S - 2 |
| Analytical element of the invention - 9 | R - 10 | I - 2 | S - 2 |
| Analytical element of the invention - 10 | R - 11 | I - 2 | S - 2 |
| Comparative analytical element - 2 | R - 12 | I - 2 | S - 2 |

With regard to analytical elements 6 to 10 of this invention and comparative analytical element 2, 10 µl each of human serums having different uric acid concentration was dropwise applied on the spreading layers in the same manner as in Example 1 and, after incubation for 7 minutes at 37° C., the reflection density was measured from the support side with use of a filter of 546 nm in respect of analytical elements 6 to 10, and filter of 650 nm in respect of comparative analytical element.

As a result, it was revealed that analytical elements 6 to 10 of this invention show better color density difference against the difference in the uric acid concentration as compared with comparative analytical element 2, proving a higher discrimination ability or determination sensitivity.

EXAMPLE 3

(Total cholesterol analytical element)

On a transparent polyethylene terephthalate film having been subjected to a subbing treatment and having a film thickness of 180 µm, a reagent layer having the composition as shown in Table 6, an intermediate layer or reagent layer as shown in Table 7 and a spreading layer having the composition as shown in Table 8 were provided in succession to produce each of analytical elements 11 to 15 of this invention and comparative analytical elements 2 and 4 as shown in Table 9.

TABLE 6

| | | Reagent layer | | | | | |
|---|---|---|---|---|---|---|---|
| | | R-13 | R-14 | R-15 | R-16 | R-17 | R-18 |
| Compound of the invention 1-1 | (g/m$^2$) | 4.98 | — | — | — | — | — |
| Compound of the invention 1-4 | (g/m$^2$) | — | 3.83 | — | — | — | — |
| Compound of the invention 1-22 | (g/m$^2$) | — | — | 4.58 | — | — | — |
| Compound of the invention 1-32 | (g/m$^2$) | — | — | — | 4.40 | — | — |
| Compound of the invention 1-37 | (g/m$^2$) | — | — | — | — | 5.55 | — |
| Comparative compound (1) | (g/m$^2$) | — | — | — | — | — | 5.98 |
| Dibutyl phthalate | (g/m$^2$) | 2.49 | 1.92 | 2.29 | 2.20 | 2.78 | 2.99 |
| Gelatin | (g/m$^2$) | 16.5 | 16.5 | 16.5 | 16.5 | 16.5 | 16.5 |
| Peroxidase | (U/m$^2$) | 12,500 | 12,500 | 12,500 | 12,500 | 12,500 | 12,500 |
| Potassium phosphate buffer, pH 6.8 | (g/m$^2$) | 3.25 | 3.25 | 3.25 | 3.25 | 3.25 | 3.25 |
| Sodium triisopropylnaphthalene-sulfonate | (g/m$^2$) | 0.93 | 0.93 | 0.93 | 0.93 | 0.93 | 0.93 |
| 1,2-Bis(vinylsulfonyl)ethane | (g/m$^2$) | 0.11 | 0.11 | 0.11 | 0.11 | 0.11 | 0.11 |
| Sodium azide | (g/m$^2$) | 0.18 | 0.18 | 0.18 | 0.18 | 0.18 | 0.18 |

*7) All of compounds 11, 1-4, 1-22, 1-32 and 1-37 and comparative compound (1) were used by dispersing them in the same procedures as those described in Example 1.

TABLE 7

|  | Intermediate layer or reagent layer | |
|---|---|---|
|  | I - 3 | R - 19 |
| N-vinyl pyrrolidone/vinyl acetate copolymer (weight ratio: 2:8) (g/m2) | 1.35 | 1.35 |
| Compound of the invention 2-16 (p-toluenesulfonate) (g/m$^2$) | — | 0.14 |
| Dimedone | — | 1.75 |

TABLE 8

|  |  | Spreading layer *(3) | |
|---|---|---|---|
|  |  | S - 3 | S - 4 |
| Fiber for filter paper material [Toyo Roshi K. K.; 40 to 100 mesh] | (g/m$^2$) | 91.0 | 91.0 |
| Styrene/glycidyl methacrylate copolymer (weight ratio: 9:1) | (g/m$^2$) | 23.0 | 23.0 |
| Polyoxyethylene monolaurate | | 11.7 | 11.7 |
| Compound of the invention 2-16 (Hydrochloride) | (g/m$^2$) | — | 0.14 |
| Dimedone | (g/m$^2$) | — | 1.75 |
| Cholesterol esterase | (U/m$^2$) | 2,500 | 2,500 |
| Cholesterol oxidase | (U/m$^2$) | 2,500 | 2,500 |
| Cow's serum albumin | (g/m$^2$) | 2.5 | 2.5 |

8) Cholesterol esterase and cholesterol oxidase were dissolved in water together with cow's serum albumin and coated by adding fine powder obtained after the resulting solution was freeze-dried.

TABLE 9

| Analytical element number | Reagent layer | Intermediate layer or reagent layer | Spreading layer |
|---|---|---|---|
| Analytical element of the invention - 11 | R - 13 | I - 3 | S - 4 |
| Analytical element of the invention - 12 | R - 14 | I - 3 | S - 4 |
| Analytical element of the invention - 13 | R - 15 | R - 19 | S - 3 |
| Analytical element of the invention - 14 | R - 16 | I - 3 | S - 4 |
| Analytical element of the invention - 15 | R - 17 | R - 19 | S - 3 |
| Comparative analytical element - 3 | R - 18 | I - 3 | S - 4 |
| Comparative analytical element - 4 | R - 18 | R - 19 | S - 3 |

With regard to analytical elements 11 to 15 of this invention and comparative analytical elements 3 and 4, 10 μl each of human serums having different total cholesterol concentration was dropwise applied on the spreading layers and, after incubation for 7 minutes at 37° C., the reflection density was measured from the support side with use of a filter of 546 nm to obtain the results shown in Table 10.

TABLE 10

| Total cholesterol concentration (mg/dl) | 145 | 310 | 460 |
|---|---|---|---|
| Analytical element of the invention - 11 | 0.75 | 1.36 | 1.73 |
| Analytical element of the invention - 12 | 0.78 | 1.44 | 1.82 |
| Analytical element of the invention - 13 | 0.74 | 1.29 | 1.60 |
| Analytical element of the invention - 14 | 0.76 | 1.35 | 1.71 |
| Analytical element of the invention - 15 | 0.72 | 1.28 | 1.58 |
| Comparative analytical element - 3 | 0.66 | 1.05 | 1.23 |
| Comparative analytical element - 4 | 0.67 | 1.02 | 1.17 |

As will be clear from the results shown in the above Table 10, it can be understood that analytical elements 11 to 15 of this invention show better color density difference against the difference in the total cholesterol concentration as compared with comparative analytical elements 3 and 4, proving a higher discrimination ability or determination sensitivity.

EXAMPLE 4

(Glucose analytical element)

On a transparent polyethylene terephthalate film having been subjected to a subbing treatment and having a film thickness of 180 μm, a reagent layer having the composition as shown in Table 11, an intermediate layer and a spreading layer each having the composition shown below were provided in succession to produce each of analytical elements 16 to 20 of this invention and comparative analytical element 5 as shown in Table 12.

TABLE 11

|  |  | Reagent layer | | | | | |
|---|---|---|---|---|---|---|---|
|  |  | R-20 | R-21 | R-22 | R-23 | R-24 | R-25 |
| Compound of the invention 1-3 | (g/m$^2$) | 4.50 | — | — | — | — | — |
| Compound of the invention 1-4 | (g/m$^2$) | — | 4.13 | — | — | — | — |
| Compound of the invention 1-29 | (g/m$^2$) | — | — | 4.93 | — | — | — |
| Compound of the invention 1-35 | (g/m$^2$) | — | — | — | 4.99 | — | — |
| Compound of the invention 1-56 | (g/m$^2$) | — | — | — | — | 4.57 | — |
| Comparative compound (1) | (g/m$^2$) | — | — | — | — | — | 6.44 |
| Dibutyl phthalate | (g/m$^2$) | 2.25 | 2.07 | 2.47 | 2.50 | 2.29 | 3.22 |
| Gelatin | (g/m$^2$) | 15.5 | 15.5 | 15.5 | 15.5 | 15.5 | 15.5 |
| Peroxidase | (U/m$^2$) | 33,000 | 33,000 | 33,000 | 33,000 | 33,000 | 33,000 |
| Glucose oxidase | (U/m$^2$) | 21,000 | 21,000 | 21,000 | 21,000 | 21,000 | 21,000 |
| Potassium phosphate buffer, pH 6.1 | (g/m$^2$) | 2.82 | 2.82 | 2.82 | 2.82 | 2.82 | 2.82 |
| Sodium triisopropylnaphthalene-sulfonate | (g/m$^2$) | 0.96 | 0.96 | 0.96 | 0.96 | 0.96 | 0.96 |
| Sodium azide | (g/m$^2$) | 0.11 | 0.11 | 0.11 | 0.11 | 0.11 | 0.11 |
| 1,2-Bis(vinylsulfonyl)ethane | (g/m$^2$) | 0.10 | 0.10 | 0.10 | 0.10 | 0.10 | 0.10 |

*9) All of compounds 1-3, 1-4, 1-29, 1-35 and 11-56 of this invention and comparative compound (1) were used by dissolving them in the same procedures as those described in Example 1.

| Intermediate layer (I-4): | |
|---|---|
| N-vinyl pyrrolidone/vinyl acetate copolymer (weight ratio: 2:8) | 1.40 g/m² |

| Spreading layer (S-5):*(3) | |
|---|---|
| Fiber for filter paper material (available from Toyo Roshi K.K.; 40 to 100 mesh) | 91.0 g/m² |
| Styrene/glycidyl methacrylate copolymer (weight ratio: 9:1) | 23.0 g/m² |
| Triton X-100 | 9.1 g/m² |
| Compound 2-16 of this invention (hydrochloride) | 0.15 g/m² |
| Dimedone | 1.90 g/m² |

TABLE 12

| Analytical element number | Reagent layer | Intermediate layer | Spreading layer |
|---|---|---|---|
| Analytical element of the invention - 16 | R - 20 | I - 4 | S - 5 |
| Analytical element of the invention - 17 | R - 21 | I - 4 | S - 5 |
| Analytical element of the invention - 18 | R - 22 | I - 4 | S - 5 |
| Analytical element of the invention - 19 | R - 23 | I - 4 | S - 5 |
| Analytical element of the invention - 20 | R - 24 | I - 4 | S - 5 |
| Comparative analytical element - 5 | R - 25 | I - 4 | S - 5 |

With regard to analytical elements 16 to 20 of this invention and comparative analytical element 5, 10 μl each of human serums having different glucose concentration was dropwise applied on the spreading layers in the same manner as in Example 1 and, after incubation for 7 minutes at 37° C., the reflection density was measured from the support side with use of a filter of 546 nm.

As a result, it was revealed that analytical elements 6 to 20 of this invention show better color density difference against the difference in the uric acid concentration as compared with comparative analytical element 5, proving a higher discrimination ability or determination sensitivity.

EXAMPLE 5

(Creatinine analytical element)

On a transparent polyethylene terephthalate film having been subjected to a subbing treatment and having a film thickness of 180 μm, a reagent layer having the composition as shown in Table 13, an intermediate layer I-1 and a spreading layer S-1 each described in Example 2 were provided in succession to produce each of analytical elements 21 to 23 of this invention and comparative analytical element 6 as shown in Table 14.

TABLE 13

| | | Reagent layer | | | |
|---|---|---|---|---|---|
| | | R-26 | R-27 | R-28 | R-29 |
| Compound of the invention 1-4 | (g/m²) | 2.95 | — | — | — |
| Compound of the invention 1-5 | (g/m²) | — | 3.30 | — | — |
| Compound of the invention 1-8 | (g/m²) | — | — | 2.95 | — |
| Comparative compound (1) | (g/m²) | — | — | — | 4.60 |
| Dibutyl phthalate | (g/m²) | 1.55 | 1.73 | 1.55 | 2.42 |
| Gelatin | (g/m²) | 19.0 | 19.0 | 19.0 | 19.0 |
| Creatininase | (U/m²) | 8,000 | 8,000 | 8,000 | 8,000 |
| Creatinase | (U/m²) | 6,000 | 6,000 | 6,000 | 6,000 |
| Sarcosine oxidase | (U/m²) | 10,000 | 10,000 | 10,000 | 10,000 |
| Peroxidase | (U/m²) | 7,500 | 7,500 | 7,500 | 7,500 |
| Phosphate buffer pH 8.1 | (g/m²) | 4.25 | 4.25 | 4.25 | 4.25 |
| Sodium triisopropylnaphthalene-sulfonate | (g/m²) | 0.86 | 0.86 | 0.86 | 0.86 |
| 1,2-Bis(vinylsulfonyl)ethane | (g/m²) | 0.06 | 0.06 | 0.06 | 0.06 |

TABLE 14

| Analytical element number | Reagent layer | Intermediate layer | Spreading layer |
|---|---|---|---|
| Analytical element of the invention - 21 | R - 26 | I - 1 | S - 1 |
| Analytical element of the invention - 22 | R - 27 | I - 1 | S - 1 |
| Analytical element of the invention - 23 | R - 28 | I - 1 | S - 1 |
| Comparative analytical element - 6 | R - 29 | I - 1 | S - 1 |

With regard to analytical elements 21 to 23 of this invention and comparative analytical element 6, 10 μl each of human serums having different creatinine concentration was dropwise applied on the spreading layers in the same manner as in Example 1 and, after incubation for 7 minutes at 37° C., the reflection density was measured from the support side with use of a filter of 546 nm to obtain the results shown in table 15.

TABLE 15

| Creatinine concentration (mg/dl) | 1.1 | 5.4 | 11.3 |
|---|---|---|---|
| Analytical element of the invention - 21 | 0.33 | 0.62 | 0.96 |
| Analytical element of the invention - 22 | 0.31 | 0.59 | 0.91 |
| Analytical element of the invention - 23 | 0.32 | 0.60 | 0.93 |
| Comparative analytical element - 6 | 0.28 | 0.52 | 0.72 |

As will be clear from the results shown in the above Table 15, it can be understood that analytical elements 21 to 23 of this invention show better color density difference against the difference in the creatinine concentration as compared with comparative analytical element 6, proving a higher discrimination ability or determination sensitivity.

As described in the foregoing, the analytical element of this invention can exhibit the remarkable effect that the determination sensitivity can be greatly improved.

We claim:

1. In an analytical method for determination, in a test solution, of hydrogen peroxide or a substance capable of being oxidized to form hydrogen peroxide, wherein the substance is reacted to form hydrogen peroxide, the hydrogen peroxide is subjected to a reaction sequence to form a measurable dye in an amount corresponding to the amount of hydrogen peroxide, and the amount of dye is measured and compared with a calibrated standard, the improvement comprising forming a measurable dye by applying the test solution to an analytical element comprising at least one reagent layer containing a reagent having peroxidative activity a compound represented by Formula (I) shown below, and an aromatic primary amine compound, or a salt thereof, capable of forming the measurable dye through the coupling reaction with the compound represented by Formula (I) shown below:

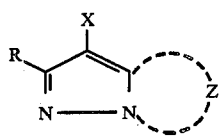

Formula (I)

wherein Z represents a group of nonmetallic atoms including at least one nitrogen necessary for forming a nitrogen-containing heterocyclic ring, which ring formed by Z may have a substituent; X represents a hydrogen atom or a group capable of being split off through the reaction with an oxidized product of the aromatic primary amine compound; and R represents a hydrogen atom or a substituent.

2. The method of claim 1, wherein said substance which is oxidized to form hydrogen peroxide is determined, said substance being oxidized by an enzyme selected from the group consisting o glucose oxidase, uricase, cholesterol oxidase, glycerol oxidase, glycerin-3-phosphate oxidase, sarcosine oxidase, pyruvate oxidase, D-amino acid oxidase, L-amino acid oxidase, L-gulono-γ-lactone oxidase, D-hydroxyacid oxidase, L-hydroxyacid oxidase, pyridoxine oxidase, hexose oxidase, o-aminophenol oxidase, amine oxidase containing pyridoxyl, amine oxidase containing flavin, xanthine oxidase, alcohol oxidase, ethanolamine oxidase, choline oxidase, acyl CoA oxidase, sulphite oxidase, and ascorbate oxidase to form an amount of hydrogen peroxide in proportion to the amount of said substance.

3. The method of claim 1, wherein said compound represented by Formula (I) is a compound represented by Formula (II) shown below:

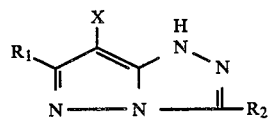

Formula (II)

wherein $R_1$, $R_2$ and X have the same meaning as R and X, respectively defined in Formula (I).

4. The method of claim 1, wherein said aromatic primary amine compound is a p-phenylenediamine compound represented by Formula (IX) shown below:

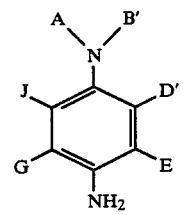

Formula (IX)

wherein A and B' each represent a hydrogen atom or an alkyl group, and A and B' may form a heterocyclic ring together with a nitrogen atom; and D', E. G and J each represent a hydrogen atom, a halogen atom, a hydroxyl group, an amino group, an alkoxy group, an acylamide group, an arylsulfonamide group, an alkylsulfonamide group or an alkyl group.

5. In an analytical element, for determination of hydrogen peroxide or a substance capable of being oxidized to form hydrogen peroxide, said analytical element comprising a support carrying at least one reagent layer including reagents for forming a measurable dye in proportion to the amount of hydrogen peroxide, reagent having peroxidative activity, a compound represented by Formula (I) shown below, and an aromatic primary amine compound, or a salt thereof, capable of forming a measurable dye through the coupling reaction with the compound represented by Formula (I) shown below:

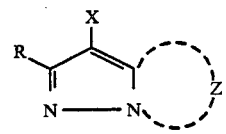

wherein Z represents a group of nonmetallic atoms including at least one nitrogen necessary for forming a nitrogen-containing heterocyclic ring, which ring formed by Z may have a substituent; X represents a hydrogen atom or a group capable of being split off through the reaction with an oxidized product of the aromatic primary amine compound; and R represents a hydrogen atom or a substituent.

6. The analytical element of claim 5, D-amino acid oxidase, L-amino acid oxidase, L-gulono-γ-lactone oxidase, D-hydroxyacid oxidase, L-hydroxyacid oxidase, pyridoxine oxidase, hexose oxidase, o-aminophenol oxidase, amine oxidase containing pyridoxyl, amine oxidase containing flavin, xanthine oxidase, alcohol oxidase, ethanolamine oxidase, choline oxidase, acyl CoA oxidase, sulphite oxidase, and ascorbate oxidase.

7. The analytical element of claim 5, wherein said compound represented by Formula (I) is a compound represented by Formula (II) shown below:

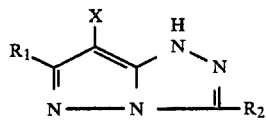

Formula (II)

wherein $R_1$, $R_2$ and X have the same meaning as R and X, respectively, defined in Formula (I).

8. The analytical element of claim 5, wherein said aromatic primary amine compound is a p-phenylenediamine compound represented by Formula (IX) shown below,

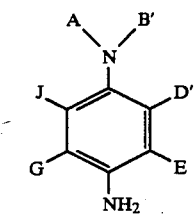

Formula (IX)

wherein A and B' each represent a hydrogen atom or an alkyl group, and A and B' may form a heterocyclic ring together with a nitrogen atom; and D', E, G and J each represent a hydrogen atom, a halogen atom, a hydroxyl group, an amino group, an alkoxy group, an acylamide group, an arylsulfonamide group, an alkylsulfonamide group or an alkyl group.

9. An analytical element, for determination of hydrogen peroxide or a substance capable of being oxidized to form hydrogen peroxide, said analytical element comprising a support having thereon a reagent layer and a porous spreading layer, and containing a reagent having peroxidative activity, a compound represented by Formula (I) shown below, and an aromatic primary amine compound, or a salt thereof, capable of forming a measurable dye through the coupling reaction with the compound represented by Formula (I) shown below, said compound represented by Formula (I) and said aromatic primary amine compound being contained in different layers,

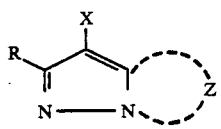

Formula (I)

wherein Z represents a group of nonmetallic atoms including at least one nitrogen necessary for forming a nitrogen-containing heterocyclic ring, which ring formed by Z may have a substituent; X represents a hydrogen atom or a group capable of being split off through the reaction with an oxidized product of the aromatic primary amine compound; and R represents a hydrogen atom or a substituent.

10. The analytical element of claim 9, further comprising an enzyme capable of oxidizing said substance to form hydrogen peroxide in an amount in proportion to the amount of said substance, wherein said enzyme is selected from the group consisting of glucose oxidase, uricase, cholesterol oxidase, glycerol oxidase, glycerin-3-phosphate oxidase, sarcosine oxidase pyruvate oxidase, D-amino acid oxidase, L-amino acid oxidase, L-gulono-γ-lactone oxidase, D-hydroxyacid oxidase, L-hydroxyacid oxidase, pyridoxine oxidase, hexose oxidase, o-aminophenol oxidase, amine oxidase containing pyridoxyl, amine oxidase containing flavin, xanthine oxidase, alcohol oxidase, ethanolamine oxidase, choline oxidase, acyl CoA oxidase, sulphite oxidase, and ascorbate oxidase.

11. The analytical element of claim 9, wherein said compound represented by Formula (I) is a compound represented by Formula (II) shown below:

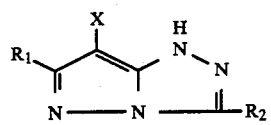

Formula (II)

wherein $R_1$, $R_2$ and X have the same meaning as R and X, respectively, defined in Formula (I).

12. The analytical element of claim 9, wherein said aromatic primary amine compound is a p-phenylenediamine compound represented by Formula (IX) shown below:

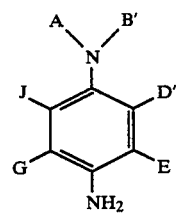

Formula (IX)

wherein A and B' each represent a hydrogen atom or an alkyl group, and A and B' may form a heterocyclic ring together with a nitrogen atom; and D', E, G and J each represent a hydrogen atom, a halogen atom, a hydroxyl group, an amino group, an alkoxy group, an acylamide group, an arylsulfonamide group, an alkylsulfonamide group or an alkyl group.

13. The analytical element of claim 9, wherein said compound represented by Formula (I) is contained in said reagent layer, and said aromatic primary amine compound is contained in said porous spreading layer.

14. In an analytical method for determination, in a test solution, of hydrogen peroxide or a substance capable of being oxidized to form hydrogen peroxide, wherein the substance is reacted to form hydrogen peroxide, the hydrogen peroxide is subjected to a reaction sequence to form a measurable dye in an amount corresponding to the amount of hydrogen peroxide, and the amount of dye is measured and compared with a calibrated standard, the improvement comprising forming a measurable dye by applying the test solution to an analytical element comprising at least one reagent layer containing an enzyme capable of oxidizing said substance to form hydrogen peroxide, a reagent having peroxidative activity, a compound represented by Formula (I) shown below, and an aromatic primary amine compound, or a salt thereof, capable of forming the measurable dye through the coupling reaction with the compound represented by Formula (I) shown below:

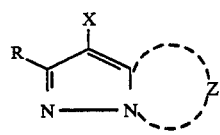

Formula (I)

wherein Z represents a group of nonmetallic atoms including at least one nitrogen necessary for forming a nitrogen-containing heterocyclic ring, which ring formed by Z may have a substituent, X represents a hydrogen atom or a group capable of being split off through the reaction with an oxidized product of the aromatic primary amine compound; and R represents a hydrogen atom or a substituent.

15. In an analytical element for determination of hydrogen peroxide or a substance capable of being oxidized to form hydrogen peroxide, said analytical element comprising a support having thereon a reagent layer and a porous spreading layer and including an enzyme capable of oxidizing said substance to form hydrogen peroxide, a reagent having peroxidative activity, and reagents for forming a measurable dye in proportion to the amount of hydrogen peroxide, wherein the improvement comprises said reagents for forming a measurable dye being a compound represented by Formula (I) shown below, and an aromatic primary amine compound, or a salt thereof, capable of forming a dye through a coupling reaction with the compound represented by Formula (I) shown below, said compound represented by Formula (I) and said aromatic primary amine compound being contained in different layers:

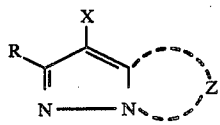 Formula (I)

wherein Z represents a group of nonmetallic atoms including at least one nitrogen necessary for forming a nitrogen-containing heterocyclic ring, which ring formed by Z may have a substituent; X represents a hydrogen atom or a group capable of being split off through the reaction with an oxidized product of the aromatic primary amine compound; and R represents a hydrogen atom or a substituent.

16. The method of claim 14, wherein said enzyme capable of oxidizing said substance to form hydrogen peroxide in proportion to the amount of said substance is selected from the group consisting of glucose oxidase, uricase, cholesterol oxidase, glycerol oxidase, glycerin-3-phosphate oxidase, sarcosine oxidase, pyruvate oxidase, D-amino acid oxidase, L-amino acid oxidase, L-gulone-γ-lactone oxidase, D-hydroxyacid oxidase, L-hydroxyacid oxidase, pyridoxine oxidase, hexose oxidase, o-aminophenol oxidase, amine oxidase containing pyridoxyl, amine oxidase containing flavin, xanthine oxidase, alcohol oxidase, ethanolamine oxidase, choline oxidase, acyl CoA oxidase, sulphite oxidase, and ascorbate oxidase.

17. The analytical element of claim 15, wherein said enzyme capable of oxidizing said substance to form hydrogen peroxide in proportion to the amount of said substance is selected from the group consisting of glucose oxidase, uricase, cholesterol oxidase, glycerol oxidase, glycerin-3-phosphate oxidase, sarcosine oxidase, pyruvate oxidase, D-amino acid oxidase, L-amino acid oxidase, L-gulono-γ-lactone oxidase, D-hydroxyacid oxidase, L-hydroxyacid oxidase, pyridoxine oxidase, hexose oxidase, o-aminophenol oxidase, amine oxidase containing pyridoxyl, amine oxidase containing flavin, xanthine oxidase, alcohol oxidase, ethanolamine oxidase, choline oxidase, acyl CoA oxidase, sulphite oxidase, and ascorbate oxidase.

18. The analytical element of claim 1 wherein said substance capable of being oxidized to form hydrogen peroxide is selected from the group consisting of glucose, uric acid, creatinine and cholesterol.

* * * * *